(12) United States Patent  
McGiboney

(10) Patent No.: US 8,816,242 B2  
(45) Date of Patent: Aug. 26, 2014

(54) METHOD OF FABRICATING IMPLANTABLE PULSE GENERATOR USING WIRE CONNECTIONS TO FEEDTHROUGH STRUCTURES AND IMPLANTABLE PULSE GENERATORS

(75) Inventor: Ken McGiboney, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 604 days.

(21) Appl. No.: 13/076,858

(22) Filed: Mar. 31, 2011

(65) Prior Publication Data

US 2011/0245894 A1 Oct. 6, 2011

Related U.S. Application Data

(60) Provisional application No. 61/319,679, filed on Mar. 31, 2010.

(51) Int. Cl.
  *B23K 26/32* (2014.01)
  *B23K 11/16* (2006.01)
  *A61N 1/375* (2006.01)

(52) U.S. Cl.
  CPC .............. *A61N 1/3754* (2013.01); *B23K 26/32* (2013.01); *B23K 2201/38* (2013.01)
  USPC ................................ 219/121.64; 219/117.1

(58) Field of Classification Search
  CPC .... B23K 2201/38; B23K 26/32; B23K 26/20; B23K 11/002; A61N 1/3754
  USPC .......................... 219/121.64, 117.1; 228/173.1
  See application file for complete search history.

(56) References Cited

U.S. PATENT DOCUMENTS

| 4,220,814 | A | | 9/1980 | Cook et al. |
|---|---|---|---|---|
| 4,692,121 | A | * | 9/1987 | Arbogast, Jr. ................. 439/874 |
| 5,118,916 | A | * | 6/1992 | Hucik ......................... 219/117.1 |
| 5,163,221 | A | * | 11/1992 | Favre-Tissot et al. ..... 219/117.1 |
| 5,272,283 | A | | 12/1993 | Kuzma |
| 5,300,755 | A | * | 4/1994 | Nishitani et al. ......... 219/121.64 |
| 5,541,365 | A | * | 7/1996 | Sugiura et al. ........... 219/121.64 |
| 5,571,146 | A | | 11/1996 | Jones et al. |
| 5,935,463 | A | * | 8/1999 | Sugiura .................... 219/121.64 |
| 5,977,508 | A | * | 11/1999 | Takano ...................... 219/117.1 |
| 6,264,510 | B1 | * | 7/2001 | Onizuka et al. ............... 439/876 |
| 7,444,180 | B2 | | 10/2008 | Kuzma et al. |
| 7,594,828 | B2 | | 9/2009 | Alexander et al. |
| 7,736,191 | B1 | | 6/2010 | Sochor |
| 2005/0085870 | A1 | | 4/2005 | Goroszeniuk |
| 2005/0246006 | A1 | | 11/2005 | Daniels |
| 2006/0221543 | A1 | | 10/2006 | Stevenson |
| 2008/0046051 | A1 | * | 2/2008 | Skubitz et al. ................. 607/115 |

(Continued)

*Primary Examiner* — Geoffrey S Evans

(57) ABSTRACT

A method of fabricating an implantable pulse generator for generating electrical pulses for application to tissue of a patient, the method comprises: providing one or more housing components adapted to house at least pulse generating and switching circuitry of the implantable pulse generator; providing a feedthrough assembly adapted to be coupled with the one or more housing components, the feedthrough assembly comprising an array of feedthrough pins for providing respective electrical connections from a hermetically sealed enclosure formed within the one or more housing components to a location exterior to the enclosure; providing a plurality of welding components with each welding component comprising a first portion adapted to engage a respective feedthrough pin and a second portion for engaging a conductor wire; performing one or more weld operations for each welding component to connect each welding component with a respective feedthrough pin and a respective conductor wire.

9 Claims, 6 Drawing Sheets

(56) References Cited

U.S. PATENT DOCUMENTS

| | | | |
|---|---|---|---|
| 2008/0071320 A1* | 3/2008 | Brase | 607/37 |
| 2009/0203258 A1* | 8/2009 | Guenther et al. | 439/587 |
| 2010/0030296 A1* | 2/2010 | Rundle et al. | 607/37 |
| 2010/0179627 A1 | 7/2010 | Floyd et al. | |
| 2010/0256695 A1* | 10/2010 | Iyer et al. | 607/2 |

* cited by examiner

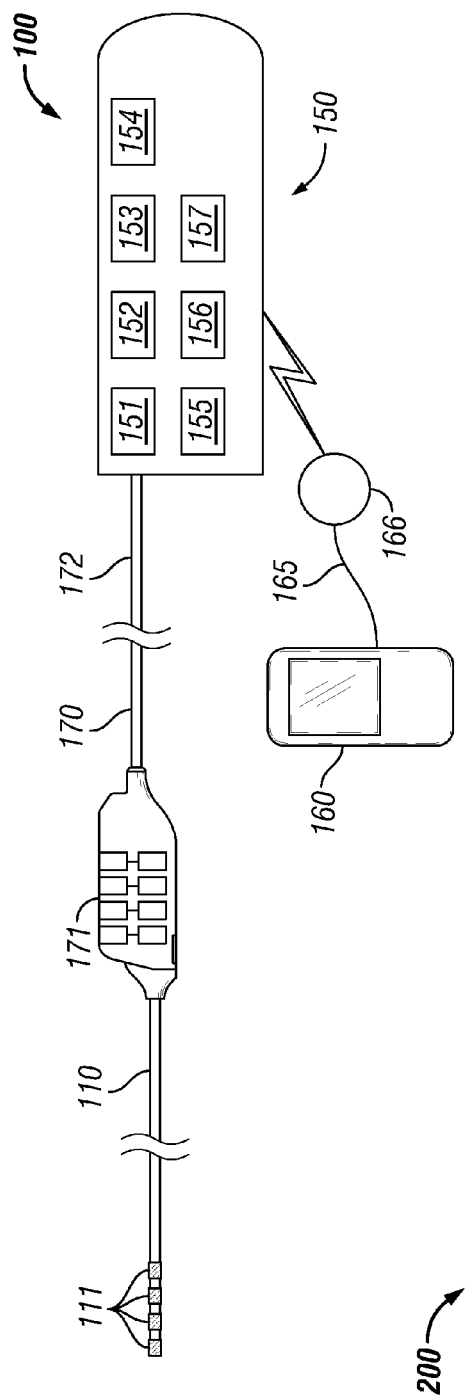
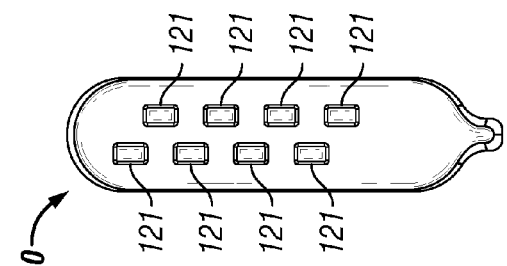
FIG. 1
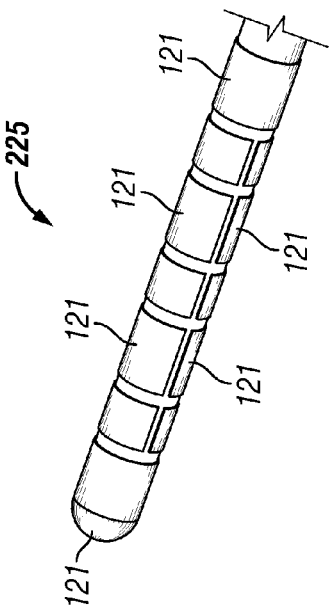
FIG. 2B
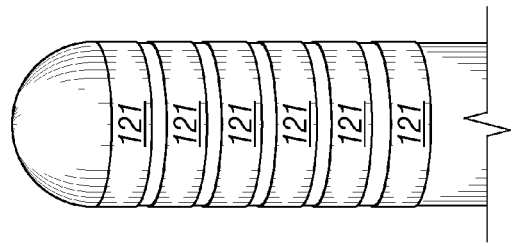

METHOD OF FABRICATING IMPLANTABLE PULSE GENERATOR USING WIRE CONNECTIONS TO FEEDTHROUGH STRUCTURES AND IMPLANTABLE PULSE GENERATORS

CROSS-REFERENCE TO RELATED APPLICATIONS

This application claims the benefit of U.S. Provisional Application No. 61/319,679, filed Mar. 31, 2010, which is incorporated herein by reference.

TECHNICAL FIELD

This application is generally related to a method of fabricating an implantable pulse generator using wire connections to feedthrough structures.

BACKGROUND

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

SUMMARY

In one embodiment, a method of fabricating an implantable pulse generator for generating electrical pulses for application to tissue of a patient, the method comprises: providing one or more housing components adapted to house at least pulse generating and switching circuitry of the implantable pulse generator; providing a feedthrough assembly adapted to be coupled with the one or more housing components, the feedthrough assembly comprising an array of feedthrough pins for providing respective electrical connections from a hermetically sealed enclosure formed within the one or more housing components to a location exterior to the enclosure; providing a plurality of welding components with each welding component comprising a first portion adapted to engage a respective feedthrough pin and a second portion for engaging a conductor wire; performing one or more weld operations for each welding component to connect each welding component with a respective feedthrough pin and a respective conductor wire by applying a majority of welding energy directly to the welding components; wherein, within the enclosure, each feedthrough pin is electrically coupled to the pulse generating circuitry through the switching circuitry of the implantable pulse generator.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 1 depicts a stimulation system according to one representative embodiment.

FIGS. 2A-2C respectively depict stimulation portions for inclusion at the distal end of a lead according to some representative embodiments.

DETAILED DESCRIPTION

Figure 3C:
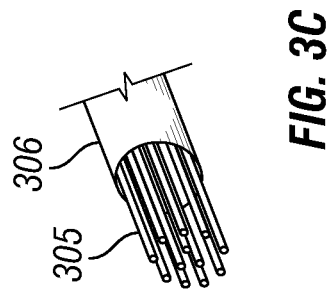
FIGS. 3A-3E depict respective components for creating an electrical connection from within the housing of a pulse generator to wire conductors of a lead body according to one representative embodiment.

FIG. 1 depicts stimulation system 100 that generates electrical pulses for application to tissue of a patient according to one embodiment. For example, system 100 may be adapted to stimulate spinal cord tissue, peripheral nerve tissue, deep brain tissue, cortical tissue, cardiac tissue, digestive tissue, pelvic floor tissue, or any other suitable tissue within a patient's body.

System 100 includes implantable pulse generator 150 that is adapted to generate electrical pulses for application to tissue of a patient. Implantable pulse generator 150 typically comprises a metallic housing that encloses controller 151, pulse generating circuitry 152, charging coil 153, battery 154, far-field and/or near field communication circuitry 155, battery charging circuitry 156, switching circuitry 157, etc. of the device. Controller 151 typically includes a microcontroller or other suitable processor for controlling the various other components of the device. Software code is typically stored in memory of the pulse generator 150 for execution by the microcontroller or processor to control the various components of the device.

In contrast to many conventional IPGs, pulse generator 150 may comprise attached extension component 170. That is, in lieu of providing a separate extension lead that is physically placed within a header of an IPG by the surgeon during implant, extension component 170 may be directly attached to and may be non-removable from pulse generator 150 according to some representative embodiments. Although the integrated extension component 170 is provided for some embodiments, extension component 170 may be separate according to other embodiments. The welding techniques and components disclosed herein may be employed within any suitable implantable pulse generating system for applying pulses to tissue of a patient. Within pulse generator 150, electrical pulses are generated by pulse generating circuitry 152 and are provided to switching circuitry 157. The switching circuit connects to output wires, traces, lines, or the like (not shown in FIG. 3) which are, in turn, electrically coupled to internal conductive wires (not shown in FIG. 3) of lead body 302 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from pulse generator 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within pulse generator 150, a processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may comprise a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Provisional Patent Application Ser. No. 61/247,360, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Although not required for all embodiments, the lead bodies of lead(s) 110 and extension component 170 may be fabricated to flex and elongate in response to patient movements upon implantation within the patient. By fabricating lead bodies according to some embodiments manner, a lead body or a portion thereof is capable of elastic elongation under relatively low stretching forces. Also, after removal of the stretching force, the lead body is capable of resuming its original length and profile. For example, the lead body may stretch 10%, 20%, 25%, 35%, or even up or above to 50% at forces of about 0.5, 1.0, and/or 2.0 pounds of stretching force.

The ability to elongate at relatively low forces may present one or more advantages for implantation in a patient. For example, as a patient changes posture (e.g., "bends" the patient's back), the distance from the implanted pulse generator to the stimulation target location changes. The lead body may elongate in response to such changes in posture without damaging the conductors of the lead body or disconnecting from pulse generator. Also, deep brain stimulation implants, cortical stimulation implants, and occipital subcutaneous stimulation implants usually involve tunneling of the lead body through tissue of the patient's neck to a location below the clavicle. Movement of the patient's neck subjects a stimulation lead to significant flexing and twisting which may damage the conductors of the lead body. Due to the ability to elastically elongate responsive to movement of the patient's neck, certain lead bodies according to some embodiments are better adapted for such implants than some other known lead body designs. Fabrication techniques and material characteristics for "body compliant" leads are disclosed in greater detail in U.S. Provisional Patent Application Ser. No. 60/788,518, entitled "Lead Body Manufacturing," filed Mar. 31, 2006, which is incorporated herein by reference.

Controller device 160 may be implemented to recharge battery 153 of pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery 153 by charging circuitry 154. Charging circuitry 154 may also communicate status messages to controller 160 during charging operations using pulse-loading or any other suitable technique. For example, controller 160 may communicate the coupling status, charging status, charge completion status, etc.

External controller device 160 is also a device that permits the operations of pulse generator 150 to be controlled by user after pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

FIGS. 3A-3E depict respective components for creating an electrical connection from within the housing of a pulse generator to wire conductors of a lead body according to one representative embodiment.

Figure 3B:
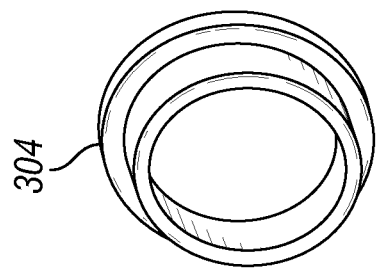
Figure 3E:
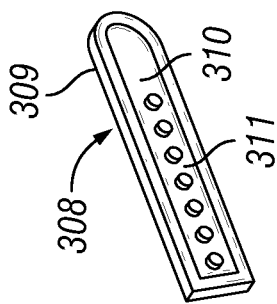
Figure 3A:
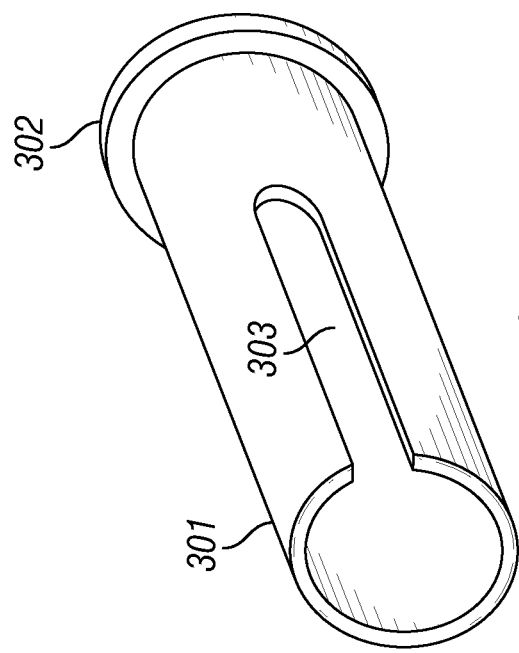
Figure 3D:
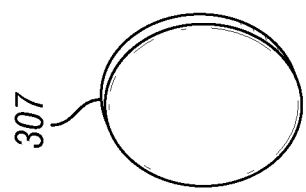

FIG. 3A depicts tube 301. Although shown as a cylindrical structure in FIG. 3A, tube 301 may alternatively possess any other suitable cross-sectional shape (e.g., oval, rectangular, etc.). Tube 301 comprises slot 303 and, optionally, flange 302. FIG. 3B depicts end piece 304. FIG. 3D depicts cap structure 307. Tube 301, end piece 304, and cap 307 are preferably fabricated from the same type of material as employed for the material of the "can" or housing of pulse generator 150 (or, alternatively, a metallurgically compatible material). For example, suitable titanium materials or alloys may be employed for one or more of these components according to some embodiments. One or more of tube 301, end piece 304, and cap 307 may be fabricated using suitable metal processing techniques. For example, tube 301 may be fabricated using metal extrusion with post extrusion processing to create slot 303 and flange 302. Alternatively, metal injection molding may be employed for one or more of tube 301, end piece 304, and cap 307 depending upon the component complexity selected for a specific implementation.

FIG. 3B depicts lead body 306 that includes a plurality of conductor wires 305 within insulative material. At the proximal end of lead body, a length of each conductor wire 305 extends out from the insulative material. Lead body 306 may be fabricated using any known or later developed process. Examples of various lead body fabrication processes are disclosed in U.S. Pat. No. 6,216,045, U.S. Pat. No. 7,287,366, U.S. Patent Application Publication No. 20050027340A1, and U.S. Patent Application Publication No. 20070282411A1, which are incorporated herein by reference.

FIG. 3E depicts feedthrough assembly 308. Feedthrough assembly 308 comprises a plurality of feedthrough pins 310. Feedthrough pins 310 preferably extend through surface 311 from the "back" side of assembly 308 to the "front" side of assembly 308. In other embodiments, pins 310 need not extend through surface 311 and may be electrically coupled to one or more intermediate electrical components to extend the electrical connection through to the other side. Feedthrough assembly 300 also comprises ferrule 309 about the perimeter of assembly 300. Ferrule 309 is shaped to allow ferrule 309 to be attached to slot 303 and to allow the end of tube 301 to be sealed upon subsequent operations. Feedthrough assembly 308 may be fabricated using conventional techniques for feedthrough components, although feedthrough assembly 309 comprises a different structural design than conventional feedthrough components.

These various components are assembled and welded (e.g., using a suitable laser welding system) together to form an integrated structure before being coupled with the housing of pulse generator 150. In one embodiment, end piece 304 is placed over the insulative material of lead body 306. Then, tube 301 is likewise placed over the insulative material of lead body 306. With tube 301 placed sufficiently far along lead body 306 that it does not appreciable obstruct operations, the various wires 305 of lead body 306 are welded to respective feedthrough pins 310 (on the back side) of feedthrough assembly 308 (e.g., using the laser welding system or resistive welding). Non-conductive adhesive may also be applied to fix and reinforce the connection between wires 305 and pins 310. Tube 301 is slid back along lead body 306 such that assembly 308 is disposed in slot 303. Welding is applied to connect tube 301 to end piece 304 and to connect tube 301 to ferrule 309 of assembly 308 (preferably, using the laser welding system). In one specific embodiment, biocompatible polymer material (e.g., silicone or urethane materials) may be injected or otherwise provided within tube 301 before tube 301 is sealed through the welding to provide support for wires 305. End cap 307 is then welded to the distal end of tube 301 (preferably, using the laser welding system) to seal tube 301. A medical adhesive may also be applied where lead body 306 enters tube 301 to provide a non-hermetic seal.

Figure 4:
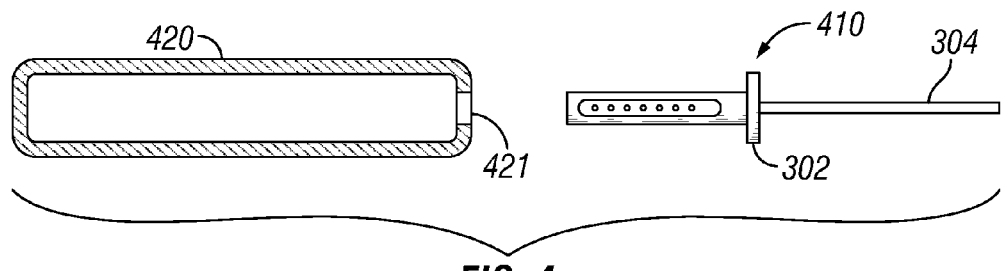
FIG. 4 depicts integration of an intermediate assembly including feedthrough structure with one or more housing component(s) of an implantable pulse generator according to one representative embodiment.

After performing the welding of these components, intermediate assembly 410 is formed (as shown in FIG. 4). Intermediate assembly 410 is then integrated with the housing component(s) 420 of pulse generator 150. Specifically, housing component(s) 420 may include an aperture 421 along one of its surfaces. Intermediate assembly 410 is placed through aperture 421 with flange 302 placed against the outer surface of housing components 420. Flange 302 is then welded to housing component(s) 420. Upon completion of the welding operations, the internal components of pulse generator 150 within housing component(s) 420 are hermetically sealed while being electrically connected to the conductive wires of lead body 306. Connector portion 171 may be provided at the proximal end of lead body 306 before or after intermediate assembly 410 is integrated with housing component(s) 420. Any suitable known or later developed technique for providing connector portion 171 may be employed.

In some embodiments, tube 301 is adapted to provide a frictional fit with lead body 306. Specifically, tube 301 may provide a sufficiently large frictional force to prevent lead body 306 from disengaging from the electrical connections formed with pins 310 feedthrough component 308 by stretching forces experienced in the patient's body after implantation. The interior surface of tube 301 may be adapted to contact lead body 306 for this purpose. The interior diameter of tube 301 may be sized to provide sufficient frictional contact. Also, crimping, swaging, or similar operations on tube 301 about lead body 306 may be employed to facilitate the desired frictional contact.

Figure 5:
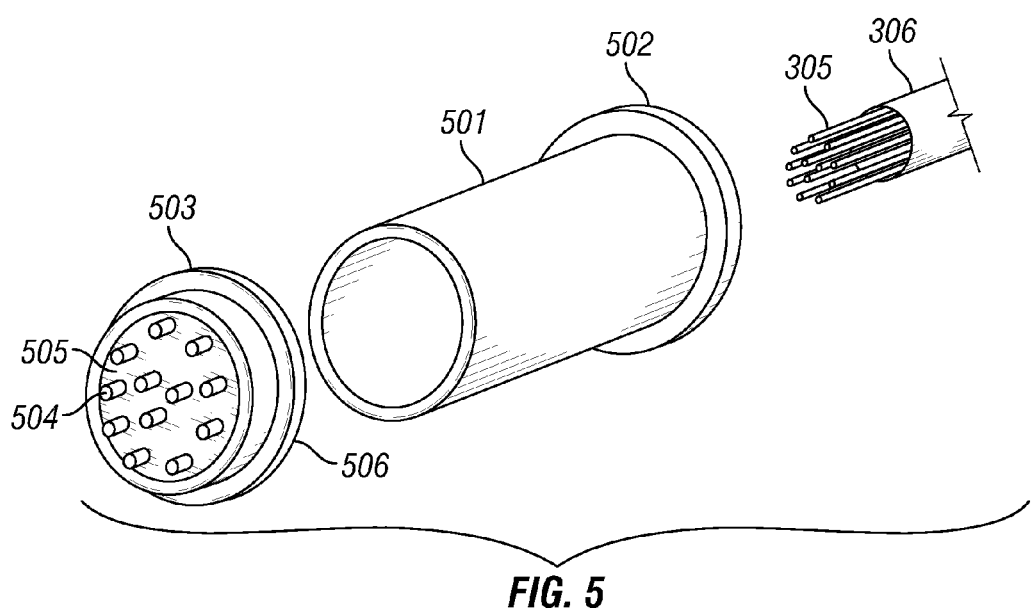
FIG. 5 depicts another plurality of components for an intermediate assembly including feedthrough structure for integration with one or more housing component(s) of an implantable pulse generator according to one representative embodiment.

FIG. 5 depicts components for an intermediate assembly of components for an extension component for integration with a pulse generator housing according to another embodiment. As shown in FIG. 5, tube 501 is a hollow, substantially cylindrical structure, although any suitable cross-sectional shape may be employed. Tube 501 includes flange 502 at its distal end. Feedthrough assembly 503 includes a plurality of conductive pins disposed through ceramic or other suitable insulative material 505. Material 505 is surrounded by metallic material of ferrule 506. Tube 501 and feedthrough assembly 503 may be fabricated using the same materials and techniques as discussed above in regard to tube 301 and feedthrough assembly 309.

During assembly, tube 501 is initially slid over wire conductors 305 of lead body 306 until tube 501 is sufficiently advanced over lead body 306 so that it does not obstruct further operations. The various wire conductors 305 of lead body 306 are coupled to respective pins 504 of feedthrough assembly 503. Pins 504 may extend through material 511 or alternatively may partially extend while being connected to intermediate electrical components. Tube 501 is the slid into position so that tube 501 is set flush against feedthrough assembly 503. Feedthrough assembly 503 is welded to tube 501 (e.g., using a laser welding system) to form an intermediate assembly. Tube 501 is then preferably back-filled with suitable biocompatible material (e.g., silicone). The intermediate assembly is placed within housing component(s) of an implantable pulse generator and is welded to the housing components to hermetically seal the implantable pulse generator.

Conventional feedthrough pins are made using approximately 0.013 inch diameter solid platinum wire with a melting temperature of 1773° C. Conductor wires 305 for lead bodies 306 commonly include seven strands (48 gauge) of MP35N where six strands are served around one of the strands thereby resulting in a diameter of approximately 0.003 inches. MP35N has a melting temperature of 1440° C. The thermal diffusivity of MP35N is approximately $2.82° C. \cdot 10^{-6}$ M$^2$/s and the thermal diffusivity of platinum is approximately $2.58° C. \cdot 10^{-5}$ M$^2$/s, a difference of approximately a factor of 10. Additionally, the individual strands of MP35N can also have a silver core, which has a melting temperature of 963° C. Further, the reflectivity of these materials to wavelengths used by laser welding systems differs. These differences in reflectivity, melting temperature, thermal diffusivity, and diameter of platinum and MP35 stranded wires contribute to the complexity of attaching wires 305 to pins 310 using laser welding.

Specifically, during a welding pulse, sufficient energy is presented to each material to create a melt zone in the metals so the metals will join together and solidify into the same mass and produce a metallurgical bond. Since platinum wire used for pins 310 is much larger and has a much greater melt temperature, the platinum wire for pins 310 requires more energy to melt than wires 305. If this amount of energy is presented to the one wire 305 positioned on the surface of a corresponding platinum pin 310 such that the laser impinges directly on the MP35N material, the wire 305 can pull away from the platinum material of pin 310 and no bond will result.

This may be caused by the fine strands of MP35N melting and the surface tension of the MP35N/silver molten material "balling up" and forming a spheroid shape thereby pulling away form the platinum material of pin 310. The process may take place before the platinum melts thereby preventing a bond from occurring. If this occurs, it is possible that the exposed portion of wire 305 may be too short to reach the platinum pin 310. If there is a long enough service loop of MP35N wire, the wire may be repositioned and another weld may be attempted. However, provision of a suitable service loop may be impossible or impractical to employ for small, precision assemblies.

Figure 6:
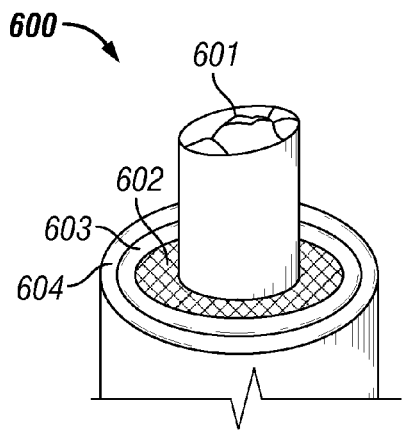
FIGS. 6 and 7 depict processing of a feedthrough pin according to one representative embodiment.
Figure 7:
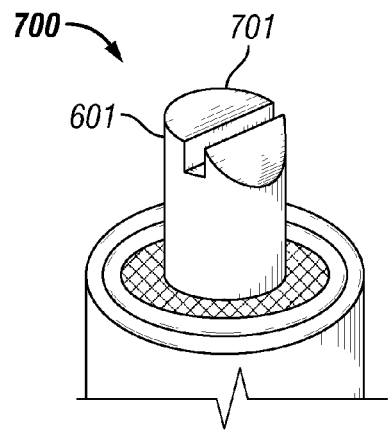

In some embodiments, one or more adaptations are provided to facilitate electrical connection of wires 305 of lead body 306 to pins 310. FIGS. 6 and 7 depict an adaptation according to one representative embodiment. FIG. 6 depicts feedthrough component 600. Feedthrough component 600 comprises platinum pin 601. Pin 601 is surrounded by gold 602 and ceramic material 603. Ferrule 604 is applied around ceramic material 603. In the state shown in FIG. 6, feedthrough component 600 may be fabricated using conventional brazing techniques. After further processing, feedthrough component 700 is provided as shown in FIG. 7. In FIG. 7, pin 601 of feedthrough component 700 comprises laser machined slot 701. Alternatively, other surface feature designs could be provided such as an "X" or cruciform-type surface feature. In one embodiment, pin 601 is initially melted using an infrared (IR) laser. While in its molten state, an ultraviolet (UV) laser is employed to laser machine pin 601 to obtain the desired surface profile and surface feature(s).

By employing the surface feature, wire 305 may be placed in slot 701 during a laser welding operation. The laser energy may be readily provided to pin 601 to melt pin 601 without inadvertently causing wire 305 to pull away before the welding operation is completed. That is, the laser energy will impinge upon pin 601 thereby melting pin 601. Wire 305 will largely be shielded from direct exposure to the laser energy by its position within slot 701 and will melt by conduction of heat from pin 601. In an alternative embodiment, a relatively lower amount of laser energy (e.g., less than the amount applied to pin 601) may be directly applied to wire 305 during the welding operation to directly heat wire 305 in addition to conductive heating.

Although only one pin 601 is shown in FIGS. 6 and 7, any suitable number of pins may be processed for a respective device. Also, the pins may be disposed in any suitable arrangement or array within a feedthrough assembly. Preferably, each pin in the feedthrough assembly is processed as discussed in regard to FIG. 7. Each slot in the pins of the feedthrough assembly may have the same orientation. Alternatively, selected slots may be oriented or "clocked" differently depending upon any constraints created by a given design of the lead body, the feedthrough assembly, housing components, or other components.

Figure 8:
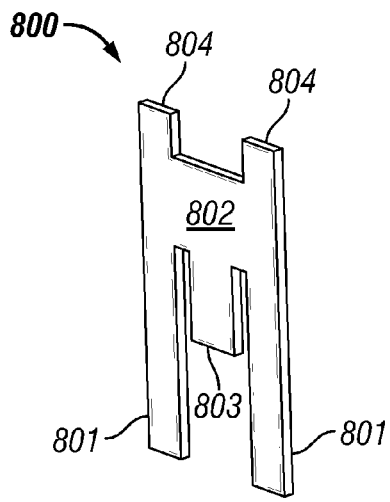
FIGS. 8-12 depict a series of structures (during various processing steps) during connection of a wire of a lead body to a feedthrough pin according to one representative embodiment.
Figure 9:
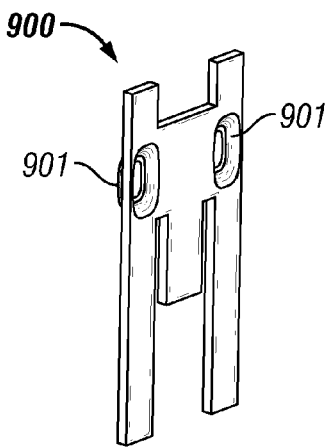

FIGS. 8-12 depict a series of structures (during various processing steps) during connection of wire 305 to pin 310 according to one representative embodiment. Selected steps shown in these FIGS. may employ conventional forming or stamping methods (e.g., using a four slide or multi-slide forming tool). In one embodiment, as shown in FIG. 8, flat platinum, platinum iridium, MP35N, or other alloy ribbon stock 800 is formed using any suitable metal forming and/or processing technique(s). Ribbon stock 800 comprises two lateral longitudinal members 801 which are joined by medial portion 802. Ribbon stock 800 further comprises central extension member 803 which extends away from medial portion 802. Also, tab members 804 on longitudinal members 801 extend above medial portion 802. In one embodiment, dimples 901 are formed in the flat stock 800 to form intermediate component 900 as shown in FIG. 9.

Figure 10:
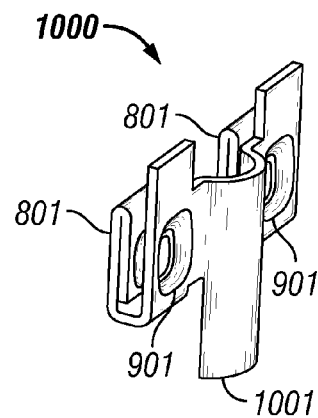

As shown in FIG. 10, the flat stock is bent upon itself to form welding component 1000. Medial member and central extension member 803 are also bent to form a curved portion 1001. The concave surface of curved portion 1001 is adapted to be placed against a feedthrough pin during subsequent operations. Extension members 801 are folded over themselves to be coplanar with the face of dimples 901.

Figure 11:
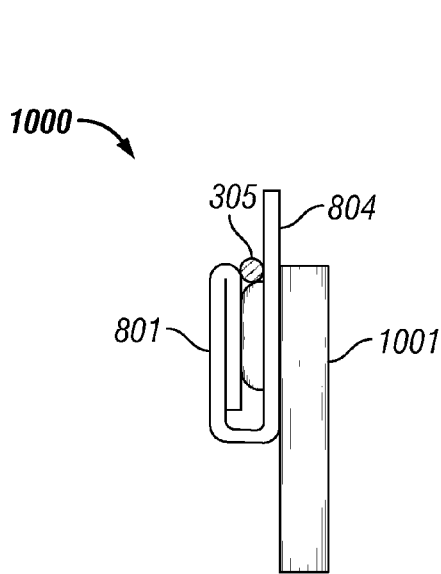
Figure 12:
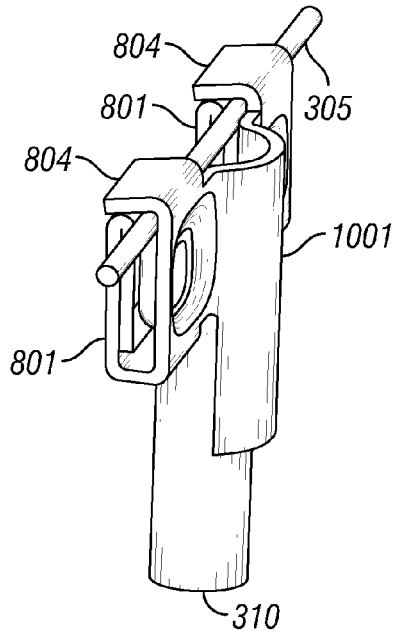

FIGS. 11 and 12 depict respective operations performed while joining wire 305 to feedthrough pin 310 (shown in FIG. 12) according to one representative embodiment.

Conductor wire 305 is placed between gap between folded longitudinal members 802 and tabs 804 as shown in FIG. 11. The size of the gap is selected to accommodate the size of wire 305 and is controlled, during the processing steps, by the depth of dimples 901. Tabs 804 are bent over wire 305 as shown in FIG. 12 to produce intimate contact between wire 305 with the surface of welding component 1000 and to retain the wire in the gap. In one embodiment, tabs 804 may apply a compressive force to wires 305 after tabs 804 are placed in position. Also, tabs 804 tend to manage the individual strands of wire 305 which may have a tendency to separate from the bundle.

In one embodiment, tabs 804 are adapted to shield wire 305 from direct exposure to the laser or resistance welder. The metal of tabs 804 may be directly heated into a molten state. For a laser weld, the laser energy may be directly focused on tabs 804 without directly impinging upon wire 305. Also, if resistance welding is employed to connect wire 305 to one or more tabs 804 of welding component 1000, the electrodes of the welder may be placed against tabs 804. Wire 305 may be heated to its melt temperature indirectly by conduction of heat from one or more of tabs 804. In this manner, wire 305 will tend to avoid pulling away and forming a spheroid mass during welding operations. Further, the tab geometry, size, thickness, and mass may be optimized for welding to wire 305. That is, the difference in energy between melting material of a respective tab 804 and melting material of wire 305 will be lessened thereby reducing the occurrence of wire 305 pulling away during a weld operation. Further, the mass per unit length of tabs 804 is relatively close (as compared to pin 310) to the mass per unit length of wire 305 which further assists successful completion of the welding process. In an alternative embodiment, a smaller amount of laser energy may be applied to wire 305 during the welding operation to directly heat wire 305 in addition to conductive heating.

During connection operations, the presence of two or more tabs 804 may enable a greater manufacturing yield. Specifically, a welding attempt preferably occurs on the tab 804 at the distal most portion of wire 305. In the event that the initial weld operation is not optimal, another weld attempt may be made on the other or next adjacent tab 804 where the wire 305 is unaffected by the first weld attempt.

The connection of welding component 1000 to pin 310 may occur independently of the connection of wire 305 to welding component 1000. Welding component 1000 may be connected to pin 310 first or wire 305 may be connected first at any suitable stage in the overall manufacturing process. As shown in FIG. 12, welding component 1000 may be placed against a respective feedthrough pin 310. Surface 1001 is preferably adapted to conform to the diameter of pin 310. Welding component 1000 may then be connected to the feedthrough pin 310 using any suitable technique including resistive welding and laser welding.

In some embodiments, welding component 1000 further enables tabs 804 to be "clocked" in any suitable orientation to aid guiding wire 305 into the gap between the tabs 804. To reduce the overall package size, the ability to orient tabs 804 in this manner aids in management of the wires 305, because the various wires 305 of lead body 306 will emanate from lead body 306 at different angles.

Figure 13:
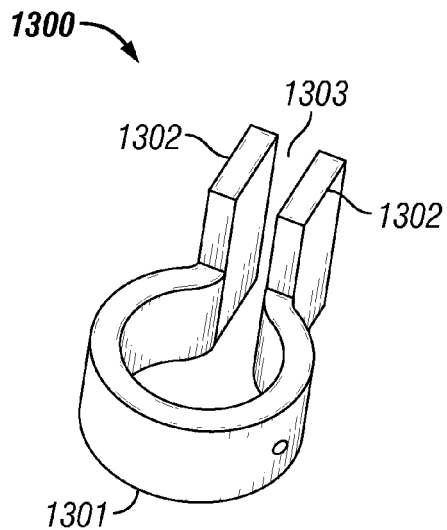
FIGS. 13-15 depict electrical connection of a respective wire of a lead body to a feedthrough pin according to another representative embodiment.
Figure 15:
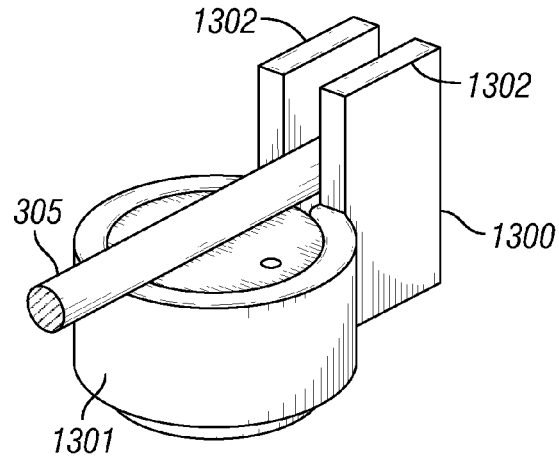
Figure 14:
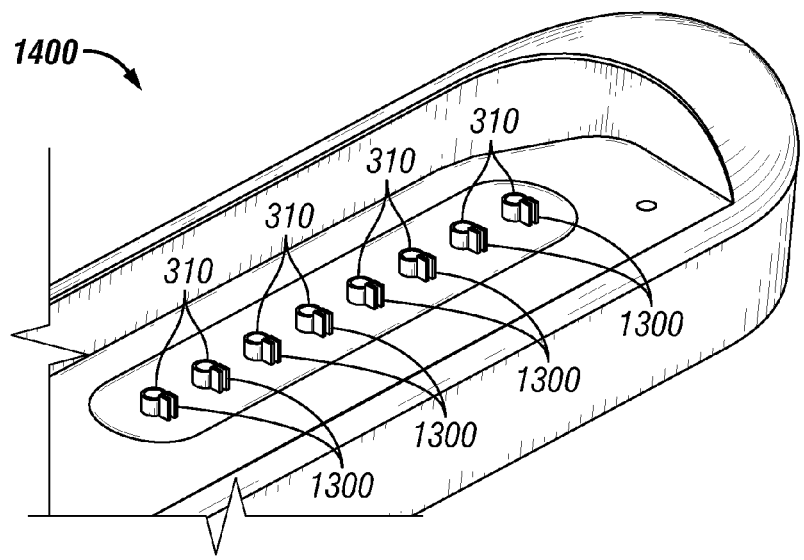

FIGS. 13-15 depict electrical connection of a respective wire 305 to a feedthrough pin 310 according to another representative embodiment. As shown in FIG. 13, ribbon clamp component 1300 is formed using conventional forming or stamping methods (e.g., using a four slide or multi-slide forming tool). Ribbon clamp component 1300 may be formed from platinum, platinum iridium, MP35N, or any other suitable alloy. Ribbon clamp component 1300 comprises curved portion 1301. Ribbon clamp component 1300 further comprises flat tab portions 1302 connected to and integral with curved portion 1301. Flat tab portions 1302 extend outward in an approximately radial direction. Also, flat tab portions 1302 are disposed adjacent to each other with gap 1303 provided between their interior surfaces. Gap 1303 is preferably sized to fit passage of wire 305 between flat tab portions 1302.

In use, a plurality of ribbon clamp components 1300 may be placed about respective feedthrough pins 310 as shown in FIG. 14. Preferably, the inner diameter of curved portion 1301 is selected according to the outer diameter of feedthrough pins 310 to facilitate this step. The band shape of curved portion 1301 facilitates locating ribbon clamp components 1300 on pins 310 and assists holding them in place so components 1300 function in a self-fixturing manner. Flat tab portions 1302 may be placed in any suitable orientation about pin axis to account for different wire angles from lead body 306 which assists assembly in reduced package-design devices. Each ribbon clamp component 1300 is preferably welded to its respective pin 310 (e.g., using laser welding or resistive welding).

A respective wire 305 is also placed within gap 1303 between flat tab portions 1302 of each ribbon clamp component 1300. After placement of the wire 305, flat tab portions 1302 may be bent around and against the wire 305 to produce intimate contact and to retain wire 305 in gap 1303. Also, flat tab portions 1302 assist in managing the individual strands of wire 305 which may have a tendency to separate from the bundle. Preferably, at this point, flat tab portions 1302 apply a compressive force to wire 305.

In one embodiment, flat tab portions 1302 are adapted to shield wire 305 from direct exposure to the laser or resistance welder. The metal of flat tab portions 1302 may be directly heated into a molten state. For a laser weld, the laser energy may be directly focused on flat tab portions 1302 without directly impinging upon wire 305. Also, if resistance welding is employed to connect wire 305 to flat tab portions 1302 of welding component 1300, the electrodes of the welder may be placed again flat tab portions 1302. Wire 305 may be heated to its melt temperature indirectly by conduction of heat from flat tab portions 1302. In this manner, wire 305 will tend to avoid pulling away and forming a spheroid mass during welding operations. Further, the tab geometry, size, thickness, and mass may be optimized for welding to wire 305. That is, the difference in energy between melting material of flat tab portions 1302 and melting material of wire 305 will be lessened thereby reducing the occurrence of wire 305 pulling away during a weld operation. Further, the mass per unit length of flat tab portions 1302 is relatively close (as compared to pin 310) to the mass per unit length of wire 305 which further assists successful completion of the welding process.

The welding of a respective component 1300 to a corresponding pin 310 and welding of the component 1300 to a corresponding wire 305 may occur in the same step. Alternatively, the welding of these elements may occur at separate times during the overall device fabrication process.

In other embodiments, welding components 1000 and 1300 providing additional geometry for reworking bad or failed weld joints. Specifically, the more complex geometry of weld components 1000 and 1300 as compared to the cylindrical shape of the feedthrough pin provides additional locations for further weld attempts to bond the wire to the feedthrough pin after an unsuccessful initial weld operation.

Figure 16A:
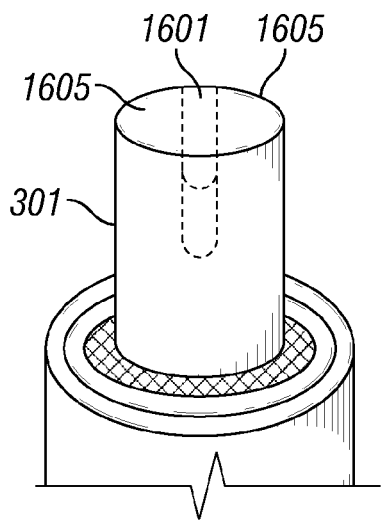
FIGS. 16A-16F depict processing of a feedthrough pin during creation of an electrical connection with a conductor wire according to one representative embodiment.
Figure 16B:
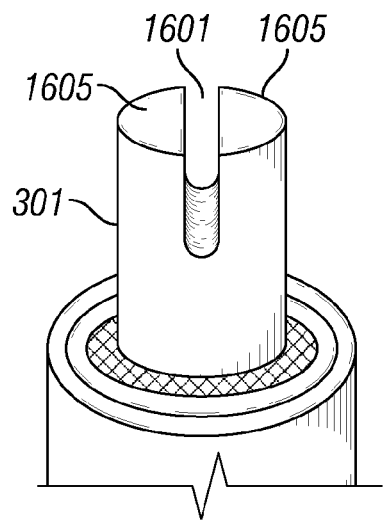

FIGS. 16A-16F depict processing of feedthrough pin 310 during creation of an electrical connection with conductor wire 305 for a pulse generator according to one representative embodiment. The process described for FIGS. 16A-16F is similar to the process discussed for FIGS. 6 and 7 with modifications. Any of the techniques discussed above may also be employed for the described below for FIGS. 16A-16F. In FIG. 16A, conventional brazed feedthrough pin 310 is shown. The pin 310 may be cut to a defined length using a UV laser. The laser cutting operation also preferably creates a flat surface on pin 310. Notch 1601 in pin 310 is made along an axis to accommodate a conductor wire as shown in FIG. 16B (e.g., using the same UV laser). Posts 1605 are defined on either side of notch 1601 by the removal of the material from pin 310 during the laser machining operation. In one embodiment, notch 1601 is formed slightly wider (e.g., 0.001 inches wider) than the outer diameter of the conductor wire to be connected to pin 310. In one embodiment, the depth of notch 1601 is approximately twice the outer diameter of the conductor wire to facilitate subsequent operations.

Figure 16C:
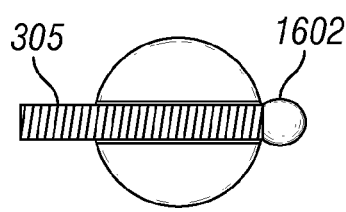

At a suitable time, preferably prior to placement of conductor 305 within notch 1601, the end of stranded conductor wire 305 is melted using a YAG laser welding system. This welding operation is performed using a sufficiently large laser beam to include the full diameter of wire 305. This welding operation forms a single ball of metal at the end of wire 305 from the strands of the DFT wire. The wire 305 is placed within notch 1601 of pin 310 with ball 1602 disposed outside the end of notch 1601 and adjacent to the exterior surface of pin 310 as shown in FIG. 16C. Posts 1605 are preferably then pinched together to clasp about wire 305. The pinching operation preferably applies a compressive force to wire 305. The distal edges of posts 1605 above wire 305 are brought into contact with each other as shown in FIG. 16D.

Figure 16D:
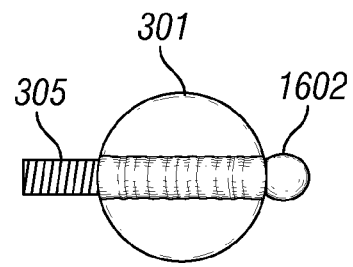
Figure 16E:
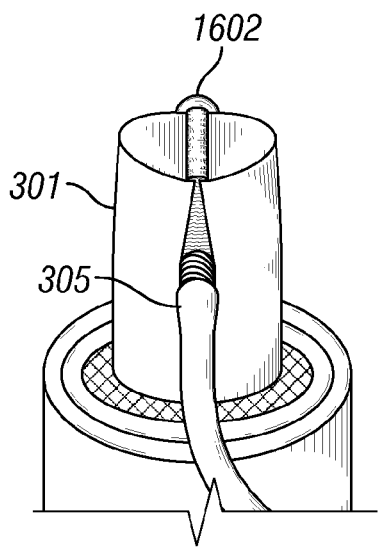
Figure 16F:
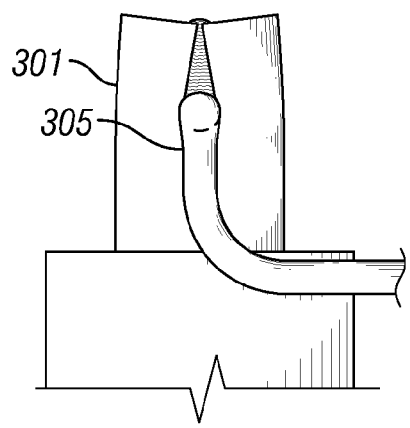

Using a YAG laser welding system, posts 1605 are seam welded together as also shown in FIG. 16D. FIGS. 16E and 16F depict different perspective views of pin 310 with wire 305 after the seam welding. The laser path preferably extends from just beyond the edge of posts 1065 on the pre-formed ball 1602 of wire 305. As the seam weld progresses, ball 1062 and pin 310 will bond making an electrical contact. Also, the seam will secure posts 1605 about the portion of wire 305 subject to a compressive force by posts 1605. Wire 305 is thereby held in place by pinched posts 1605 and the laser weld formed by ball 1062 at the end of wire 305 with pin 310. The combination of these characteristics provide a robust electrical contact and a securely held wire 305.

Alternative laser systems may be employed for any of the embodiments discussed herein. For example, a picosecond or femtosecond laser system may be employed to cut and machine pin 310 using extremely short pulses. In lieu of a YAG laser system, a fiber laser may be employed using IR wavelengths. Also, although certain discussions have include example order of processing steps, any suitable order of processing and assembly of the various components during pulse generator fabrication may be employed according to some embodiments.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of fabricating an implantable pulse generator for generating electrical pulses for application to tissue of a patient, the method comprising:
   providing one or more housing components adapted to house at least pulse generating and switching circuitry of the implantable pulse generator;
   providing a feedthrough assembly adapted to be coupled with the one or more housing components, the feedthrough assembly comprising an array of feedthrough pins for providing respective electrical connections from a hermetically sealed enclosure formed within the one or more housing components to a location exterior to the enclosure;
   providing a plurality of welding components with each welding component comprising a first portion adapted to engage a respective feedthrough pin and a second portion for engaging a conductor wire, wherein the first portion is curved to form a flush surface against a respective feedthrough pin and wherein the second portion comprises multiple flat tabs;
   bending flat tabs of the plurality of welding components to hold respective conductors extending from a lead body of insulative material;
   performing one or more weld operations for each welding component, after performing the bending, to connect each welding component with a respective feedthrough pin and a respective conductor wire from the lead body by applying a majority of welding energy directly to the welding components;
   wherein, within the enclosure, each feedthrough pin is electrically coupled to the pulse generating circuitry through the switching circuitry of the implantable pulse generator;
   wherein a distal portion of the lead body is coupled to a connector component adapted to electrically connect to terminals of a stimulation lead.

2. The method of claim 1 wherein the performing one or more weld operations comprises:
   applying laser energy to the welding component wherein the welding component comprises one or more tabs adapted to shield the corresponding conductor wire of the welding component from direct exposure to the applied laser shield.

3. The method of claim 1 wherein the performing one or more weld operations comprises:
   contacting electrodes of a resistance welding system against tabs of a welding component without directly contacting the corresponding conductor wire of the welding component.

4. The method of claim 1 further comprising:
   adjusting an orientation of tabs of one of the welding components according to an orientation of its corresponding wire.

5. The method of claim 1 wherein the performing one or more weld operations comprises:
   performing a first weld operation to weld the welding component to its corresponding feedthrough pin;
   performing a second weld operation to weld the welding component to its corresponding conductor wire.

6. The method of claim 1 wherein each welding component is welded to its corresponding feedthrough pin and its corresponding conductor wire in a substantially simultaneous manner.

7. The method of claim 1 wherein the performing one or more weld operations causes each conductor wire to melt by conduction of heat from its corresponding welding component.

8. The method of claim 1 wherein each welding component comprises:
   an indent adjacent to a tab structure for receiving a conductor wire.

9. The method of claim 1 wherein the performing one or more weld operations comprises:
   attempting a first weld operation on a first tab of one of the weld components to weld to a corresponding conductor wire at an end portion of the conductor wire; and
   performing a second weld operation, upon unsuccessful completion of the first weld operation, on a second tab of the one of the weld components to weld to the corresponding conductor wire at a relatively medial portion of the conductor wire.

* * * * *